United States Patent
Keall et al.

(10) Patent No.: US 9,314,219 B2
(45) Date of Patent: Apr. 19, 2016

(54) METHOD TO ESTIMATE REAL-TIME ROTATION AND TRANSLATION OF A TARGET WITH A SINGLE X-RAY IMAGER

(71) Applicants: Paul J Keall, Greenwich (AU); Joubin Nasehi Tehrani, Toronto (CA); Ricky O'Brien, Rozelle (AU); Per Rugaard Poulsen, Aabyhoej (DK)

(72) Inventors: Paul J Keall, Greenwich (AU); Joubin Nasehi Tehrani, Toronto (CA); Ricky O'Brien, Rozelle (AU); Per Rugaard Poulsen, Aabyhoej (DK)

( * ) Notice: Subject to any disclaimer, the term of this patent is extended or adjusted under 35 U.S.C. 154(b) by 145 days.

(21) Appl. No.: 14/102,201

(22) Filed: Dec. 10, 2013

(65) Prior Publication Data

US 2014/0241497 A1     Aug. 28, 2014

Related U.S. Application Data

(60) Provisional application No. 61/770,103, filed on Feb. 27, 2013.

(51) Int. Cl.
| | |
|---|---|
| *A61N 5/10* | (2006.01) |
| *A61B 6/00* | (2006.01) |
| *G06T 7/00* | (2006.01) |
| *A61B 6/12* | (2006.01) |

(52) U.S. Cl.
CPC .............. *A61B 6/5217* (2013.01); *A61B 6/54* (2013.01); *A61N 5/1049* (2013.01); *G06T 7/0028* (2013.01); *A61B 6/12* (2013.01); *A61N 5/103* (2013.01); *G06T 2207/10116* (2013.01); *G06T 2207/30081* (2013.01)

(58) Field of Classification Search
CPC ........................................................ A61N 5/10
See application file for complete search history.

(56) References Cited

U.S. PATENT DOCUMENTS

| | | | | |
|---|---|---|---|---|
| 5,715,166 | A  * | 2/1998 | Besl et al. ..................... | 700/182 |
| 7,929,775 | B2 * | 4/2011 | Hager ................ | G06K 9/00208 |
| | | | | 382/154 |
| 2005/0286767 | A1* | 12/2005 | Hager ................ | G06K 9/00208 |
| | | | | 382/190 |
| 2007/0135803 | A1* | 6/2007 | Belson ............................ | 606/1 |

* cited by examiner

*Primary Examiner* — Thomas R Artman
(74) *Attorney, Agent, or Firm* — Lumen Patent Firm (57) ABSTRACT

A method of real-time estimation of target rotation and translation for 6 degrees of freedom using a single planar 2-dimensional imager and an algorithm, such as the iterative closest point (ICP) algorithm, that includes creating pairing, using a nearest neighbor algorithm, between a set of target points of at least three fiducial markers and a set of source points of the markers using K nearest neighbors, iteratively executing estimation of a rotation parameter R and a translation parameter T of the markers using a cost function such as root mean square error, terminating the estimation of R and T if the change in a mean distance between the set of target points of the markers and the set of source points of the markers is below a threshold or at a maximum iteration number, transforming the set of target points of the markers using estimated parameters, and re-associating a new set of the target points of the markers.

12 Claims, 10 Drawing Sheets

METHOD TO ESTIMATE REAL-TIME ROTATION AND TRANSLATION OF A TARGET WITH A SINGLE X-RAY IMAGER

CROSS-REFERENCE TO RELATED APPLICATIONS

This application claims priority from U.S. Provisional Patent Application 61/770,103 filed Feb. 27, 2013, which is incorporated herein by reference.

FIELD OF THE INVENTION

The present invention relates generally to radiotherapy. More particularly, the invention relates to a method using a single x-ray imager to determine the 6D target translational and rotational motion in real-time.

BACKGROUND OF THE INVENTION

Radiotherapy is used to treat 40% of cancer patients in Australia and up to 55% of cancer patients in other countries. Patient motion, from the respiratory, cardiac, musculoskeletal, gastrointestinal and genitourinary systems move the tumour during a radiation treatment, which typically takes 1-30 minutes. Movement of the tumour means a misalignment of the radiation beam and tumour. This misalignment causes a loss of treatment efficacy resulting in a lower chance of tumour control, and an increase in treatment related side effects. Much effort is being put into developing methods to mitigate the effects of tumour translational motion. However, evidence shows that tumour rotation is also deleterious to treatment accuracy.

Image guided radiotherapy (IGRT) using onboard kilovoltage imager is an effective localization method to reduce the uncertainties in the estimation of tumor location and aids in patient positioning. IGRT has also been used for monitoring the target in real-time during radiation delivery. As it is difficult for the 2D kilovoltage (kV) imaging system to image soft tissue, oncologists implant radiopaque markers in the vicinity of the tumor and use the markers as indicators to determine the location of the tumor. Although IGRT is used extensively to position patients for radiotherapy treatment, tumor rotation is not currently explicitly considered during the treatment planning and delivery of radiotherapy.

In addition to prostate tumor translation, prostate tumor rotation during treatment can also affect the target dose coverage. For that reason, a small rotation may cause some part of the tumor to receive a dose that is lower than the prescribed amount. Previous studies on prostate rotation show that rotational errors are significant in some cases. The systematic uncertainty per patient for prostate rotation with 2.30°, 1.56° and 4.13° and the mean random components with 1.81°, 2.02° and 3.09° were estimated. It was also reported that the largest rotational errors occurred around the RL axis, but without preferring a certain orientation. There have been several studies to correct for tumor rotation and to reduce treatment margins for IMRT. These studies have corrected for rotation by moving or rotating the gantry, collimator, and/or couch in real-time or by using a dynamic multi leaf collimator.

What is needed is a method that estimates real-time rotation from x-ray images acquired during radiotherapy by extending translation estimation methods. One such method is to invoke iterative closest point (ICP) algorithm.

SUMMARY OF THE INVENTION

To address the needs in the art, a method of real-time estimation of target rotation and translation for 6 degrees of freedom using a single planar 2-dimensional imager and a mathematical algorithm operated by an appropriately programmed computer is provided.

According to one aspect of the invention, the mathematical algorithm is an iterative closest point (ICP) algorithm, where the ICP algorithm includes creating pairing, using a nearest neighbor algorithm on the appropriately programmed computer, between a set of target points of at least three fiducial markers and a set of source points of the at least three fiducial markers using K nearest neighbors, and iteratively executing the following: estimating a rotation parameter R and a translation parameter T of the at least three fiducial markers using a root mean square cost function; terminating the estimation of R and T if the change in a mean distance between the set of target points of the at least three fiducial markers and the set of source points of the at least three fiducial markers is below a threshold or at maximum iteration number; transforming the set of target points of the at least three fiducial markers using estimated parameters; and re-associating a new set of the target points of the at least three fiducial markers. Here, the at least three fiducial markers are disposed in a non-linear arrangement. Further, the source points of the at least three fiducial markers are generated at time $t_1$ by imaging the at least three fiducial markers using a kilovoltage imager mounted on a rotating gantry disposed to capture two dimensional images of the at least three fiducial markers, where a source position of the at least three fiducial markers is estimated using a three dimensional Gaussian probability distribution function (PDF) on the two dimensional images of the at least three fiducial markers, where a translation and rotation of the at least three fiducial markers are estimated using the PDF. In one aspect the target points of the at least three fiducial markers are generated at time $t_k$ by i) translating the source points of the at least three fiducial markers along an axis with an unknown transformation function using a translation vector T or ii) rotating the source points of the at least three fiducial markers around an axis with using a rotation matrix R or i) and ii), where a set of source points, one for each the fiducial marker, are denoted by $Q=(q_1, q_2, \ldots, q_N)$ and a set of target points, one for each the marker, are denoted by $P=(p_1, p_2, \ldots, p_N)$, where N is the number of fiducial markers, where when all the markers are translated and rotated by the same amount given by $Q(P)=sRP+T+n$, where s is a scaling factor, where n is Gaussian noise. Here, the scaling factor is determined according to a change in an area defined by the at least three fiducial markers disposed in a non-linear arrangement captured in one 2D kilovoltage (kV) image compared to a subsequent the 2D kilovoltage (kV) image. According to another aspect of the invention, the fiducial markers comprise an asymmetric shape. In a further aspect, the ICP algorithm is executed between one 2D kilovoltage (kV) image and a next the 2D kilovoltage (kV) image. Here a frequency of imaging the 2D kilovoltage (kV) image is in a range of 0.1-100 Hz.

In a further aspect of the invention, the marker positions are used to give an estimate of target deformation.

According to another aspect of the invention, the planar imager comprises a kilovoltage or megavoltage x-ray imager.

DETAILED DESCRIPTION

The current invention provides a method of using a single x-ray imager to determine the 6D target translational and rotational motion in real-time. 6D information of the target furthers the ability to deliver a dose to the target and spare surrounding healthy tissue.

Previous studies have shown that during cancer radiotherapy a small translation or rotation of the tumor can lead to errors in dose delivery. Current best practice in radiotherapy accounts for tumor translations, but is unable to address rotation due to a lack of a reliable real-time estimate. The current invention provides a method based on the iterative closest point (ICP) algorithm that can compute rotation from kilovoltage x-ray images acquired during radiation treatment delivery. In one exemplary embodiment provided, a total of 11,748 kilovoltage (kV) images were acquired from ten patients (one fraction for each patient) were used to evaluate our tumor rotation algorithm. For each kV image, the three-dimensional coordinates of three fiducial markers inside the prostate were calculated. In this example, the three-dimensional coordinates were used as input to the ICP algorithm to calculate the real-time tumor rotation and translation around three axes. The results show that the root mean square error was improved for real-time calculation of tumor displacement from a mean of 0.97 mm with the stand alone translation to a mean of 0.16 mm by adding real-time rotation and translation displacement with the ICP algorithm. The standard deviation (SD) of rotation for the ten patients was 2.3°, 0.89° and 0.72° for rotation around the right-left (RL), anterior-posterior (AP) and superior-inferior (SI) directions respectively. The correlation between all six degrees of freedom show that the highest correlation belonged to the AP and SI translation with a correlation of 0.67. The second highest correlation in the exemplary study was between the rotation around RL and rotation around AP, with a correlation of −0.33. The presented embodiment of the real-time algorithm for calculation of rotation also confirms previous studies that have shown the maximum SD belongs to AP translation and rotation around RL. ICP is a reliable and fast algorithm for estimating real-time tumor rotation, which creates a pathway to investigational clinical treatment studies requiring real-time measurement and adaptation to tumor rotation.

Applications of the current invention include cancer radiotherapy, particularly for prostate treatment and other sites where multiple landmarks, either external markers or intrinsic contrast, exists.

According to one embodiment, the invention includes a probability-based method to estimate the three dimensional target position from two dimensional projections. The current embodiment provides a real time estimate of rotation and shape deformation of the prostate during radiation therapy that can handle three or more points and use all the information available from these points. According to the current invention, a method is provided that includes an iterative closest point algorithm (ICP) (FIG. 1) to estimate rotation and also examines the maximum error level according to this estimation.

As the scale factors of the triangles formed by the markers are computed as part of the ICP algorithm, an estimate of target deformation is possible, according to one embodiment.

In a further embodiment, the algorithm can include information from imaging by the megavoltage (MV) beam used for the radiation treatment. Even for modulated beams some of the markers may be visible for some of the time. In one aspect, the use of the MV information could be used to augment the kV information. Alternately, in other embodiments the ICP method could be implemented with the MV beam alone.

A disadvantage of kV intra-treatment monitoring is the increased x-ray imaging dose. To reduce the dose, the kV information could be augmented by surface imaging (or a respiratory signal) through an internal-external model, according to another embodiment.

Turning now to the exemplary embodiment, the method includes using coordinate systems and the iterative closest point algorithm. There are many ways to represent rotation, such as: Euler angles, Gibbs vector, Cayley-Klein parameters, Pauli spin matrices, axis and angle, orthonormal matrices and Hamilton's quaternions. In the current example, Euler angles were used as it is more convenient for real-time tracking on a linac system; rotational variations about the RL, SI and AP axes are the Euler angles $\theta_{RL}$, $\theta_{SI}$ and $\theta_{AP}$, respectively.

For image acquisition, a total of 11,748 images were acquired during one fraction of the treatment of ten prostate cancer patients with radiopaque prostate markers were used in this study. Images during VMAT treatment were acquired by a kV x-ray imager mounted perpendicularly to the radiation treatment beam source (OBI, Varian Medical Systems). All treatments were dual-arc VMAT with similar treatment times and the number of images per patient was similar. The exposure parameters used were 125 kVp, 80 mA and 13 ms (a standard pelvic cone beam computed tomography scan setting) with a 6×6 cm² field size (no filter was used). The imaging frequency was 5 or 10 Hz, depending on the desired image quality. During treatment, to reduce scatter from the MV source, the kV source to detector distance was set to 180 cm (compared with 150 cm for CBCT). The estimated imaging dose for kilovoltage intrafraction imaging is 185 mGy over the course of a conventionally fractionated prostate IMRT treatment.

Figure 2:
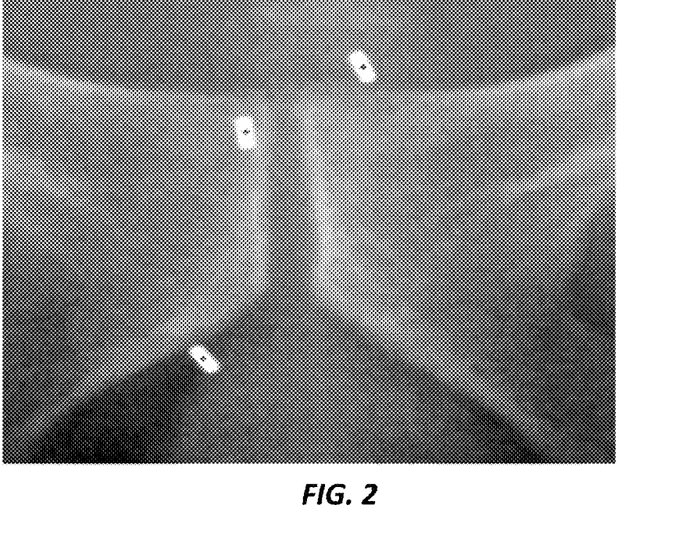
FIG. 2 shows two dimensional kV imaging of three gold radio-opaque fiducial markers implanted in the prostate of a patient. The dots within the markers indicate the location of the markers as segmented by our in-house software.

For pose estimation of fiducial markers, as the gantry rotates around the patient during treatment, two dimensional projections of the prostate are acquired at time $t_k$ by a kV imager. The fiducial markers are segmented and extracted using in-house software. FIG. 2 is a screenshot showing a kV image with three radiopaque markers and the segmented location of the markers as determined by our in-house software.

To determine the three-dimensional location of the markers from a series of two dimensional segmented markers, a three dimensional Gaussian probability distribution function (PDF) is assumed for each marker. The influence of the PDF does not affect the comparison because in both methods (three dimensional and ICP algorithm) the calculation of the PDF is the same. However, the use of the PDF itself (and errors in marker segmentation) may induce uncertainty in the rotation estimation. The covariance matrix and mean marker location used by the PDF are determined by fitting the PDF to a series of two dimensional marker locations by the maximum likelihood estimation (MLE).

Using the PDF estimated by MLE includes using an assumed 3D PDF for a 3D position of the target to determine a probability P(u, v, α) for the target to be projected into a point (u, v) on the imager positioned at angle α. Next, a probability P(u, v, α) of the 2D target position components are used in the MLE to estimate the PDF as a PDF that best fits the 2D components, where the PDF has at least one of a left-right mean position ($\mu_{LR}$), a craniocaudal mean position ($\mu_{CC}$), an anterior-posterior mean position ($\mu_{AP}$), a left-right standard deviation ($\sigma_{LR}$), a cranio-caudal standard deviation ($\sigma_{CC}$) an anterior-posterior standard deviation ($\sigma_{AP}$), a left-right—cranio-caudal correlation coefficient of motion ($\rho_{LR-CC}$), a left-right—anterior-posterior correlation coefficient of motion ($\rho_{LR-AP}$), or a craniocaudal—anterior-posterior correlation coefficient of motion ($\rho_{CC-AP}$). The PDF estimation by MLE further includes using the PDF estimated by the MLE to estimate one target position component disposed along an imager axis of the target, where an estimate of the 3D target position is made from the 2D target position components in the 2D planar image, where using the population based PDF includes using a population of 3D target position observations of a population of other targets to determine a 3D population-based PDF for the 3D position of the target, and using the 3D population-based PDF to estimate one target position component disposed along an imager axis of the target, where an estimate of the 3D target position is made from the 2D target position components in the 2D planar image. According to one embodiment of the invention, the three dimensional locations of the markers are determined from the three dimensional PDF.

For estimation of rotation and translation, assume there are two sets of data points for the fiducial markers, a source point at time $t_1$ and a target point at time $t_k$. The source points are determined during a pretreatment arc that is necessary to build the PDF needed for the translation (and rotation) estimation prior to turning the treatment beam on. The target point at time $t_k$ is obtained by rotating the source point, $t_1$, around an axis and/or translating, the source point $t_1$, along an axis with an unknown transform function. As implemented the rotation matrix of the ICP algorithm is computed about the center of mass of the markers after the shift of the translation T. The set of source points, one for each marker, are denoted by $Q=(q_1, q_2, \ldots, q_N)$ and the set of target points, one for each marker, are denoted by $P=(p_1, p_2, \ldots, p_N)$, where N is the number of fiducial markers. It is assumed that all markers are translated and rotated by the same amount, so that $$Q(P) = sRP + T + n \tag{1}$$

where R is the rotation matrix, T is the translation vector, s is the scaling factor and n is the noise (assuming the noise is Gaussian). The rotation matrix is separated into its components about each axis:

$$R = R_{RL}(\theta_{RL}) R_{SI}(\theta_{SI}) R_{AP}(\theta_{AP}) \tag{2}$$

$$R_{RL}(\theta_{RL}) = \begin{bmatrix} 1 & 0 & 0 \\ 0 & \cos(\theta_{RL}) & -\sin(\theta_{RL}) \\ 0 & \sin(\theta_{RL}) & \cos(\theta_{RL}) \end{bmatrix} \tag{3}$$

$$R_{SI}(\theta_{SI}) = \begin{bmatrix} \cos(\theta_{SI}) & 0 & \sin(\theta_{SI}) \\ 0 & 1 & 0 \\ -\sin(\theta_{SI}) & 0 & \cos(\theta_{SI}) \end{bmatrix} \tag{4}$$

$$R_{AP}(\theta_{AP}) = \begin{bmatrix} \cos(\theta_{AP}) & -\sin(\theta_{AP}) & 0 \\ \sin(\theta_{AP}) & \cos(\theta_{AP}) & 0 \\ 0 & 0 & 1 \end{bmatrix}. \tag{5}$$

Figure 1:
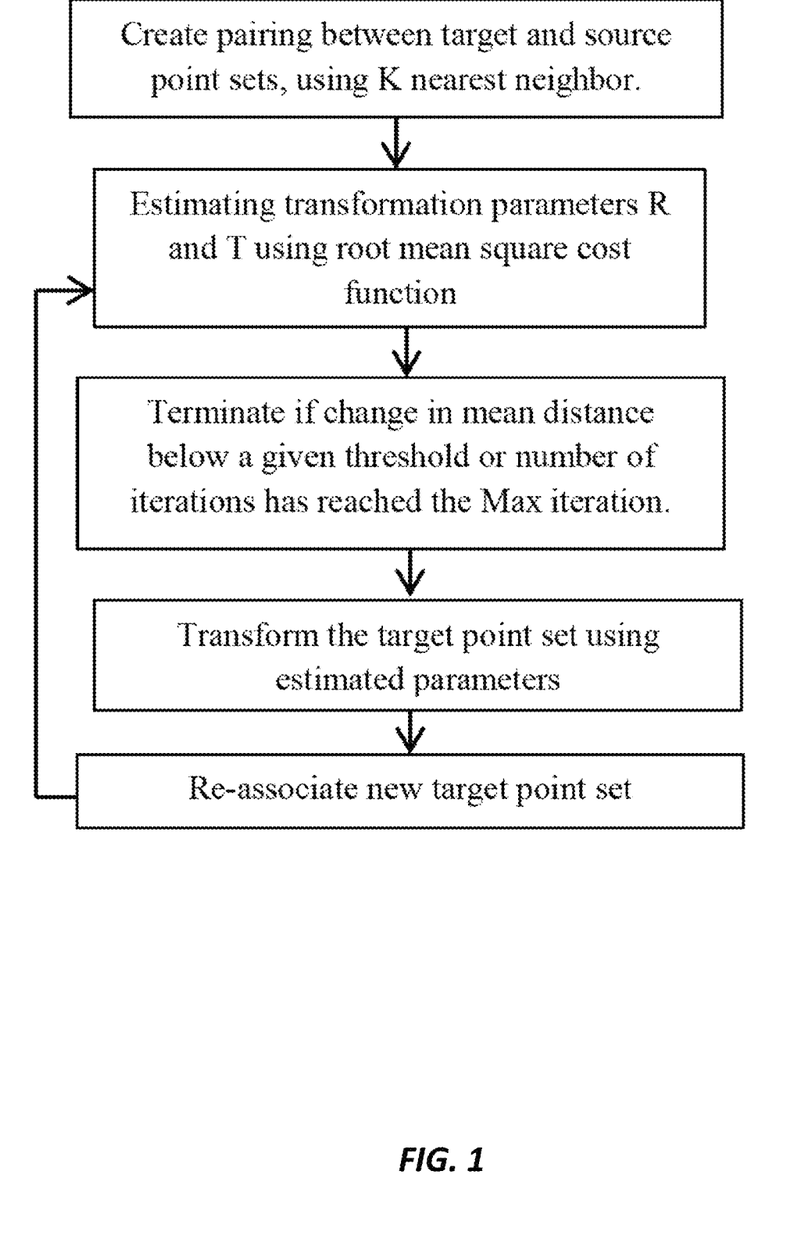
FIG. 1 shows block diagram for estimation of rotation using ICP algorithm with fiducial markers, according to one embodiment of the invention.

The ICP algorithm iteratively performs matching for every data point based on the nearest neighbor algorithm, see step 1 in FIG. 1. In this context, this step is not normally needed because it is easy to identify which marker the data point belongs to.

The nearest neighbor analysis is very important when two or more of the fiducial markers are close to each other and could be mistakenly identified. The three fiducial markers in most of the data studied here were placed sufficiently far apart to avoid mismatching. In clinical practice, either sufficient marker separation would be required or robust methods to account for the issues with overlapping markers would need to be developed. One embodiment could include using different fiducial markers of varying asymmetric shapes. In a further aspect of the invention, the marker positions are used to give an estimate of target deformation.

For step 2 in FIG. 1, the rotation and transformation matrices, R and T are estimated. To do this, the sum of the squared distances of target to source points is minimized. This forms the error function f (R, T)≈n (n is the noise in equation (1)) that is desired to minimize and is mathematically expressed as $$\underset{R,T}{\mathrm{argmin}} f(R, T, Q, P) = \frac{1}{N} \sum_{i=1}^{N} (q_i - (Rp_i + T))^2. \tag{6}$$

R and T were estimated using SVD, which is described in more detail below. Note that in equation (6) the scale factor, s, is set to 1. The scale factor will be calculated based on the area of triangles after calculating rotation and translation. The scale factor is essentially the relative area of the triangle made by the three markers. A variation in the scale could indicate errors in marker segmentation or indicate prostate deformation. During an individual fraction marker segmentation errors are more likely than prostate deformation, so the scale factor can be used as a threshold to remove suspected marker segmentation errors. Using our estimates of R and T, the values are iteratively updated using the following algorithm (step 3-5 in FIG. 1). Two intermediate matrices were used, $R_{it}$ which initially were set to the 3×3 identity matrix, and $T_{it}$ which were initially set to the 3×1 zero vector. These two matrices are updated according to $$R_{it}(k+1) = R R_{it}(k) \qquad (7)$$

$$T_{it}(k+1) = R T_{it}(K) P_k + T \qquad (8)$$

where k is the iteration number; in this case the iteration is terminated after a maximum of five iterations. In step 4 of FIG. 1, the new point $P_{k+1}$ is calculated from the new update of the following equation:

$$P_{k+1} = R_{it}(k+1) P_k + \text{repmat}(T_{it}(k+1), 1, 3) \qquad (9)$$

where repmat ($T_{it}$ (k+1), 1, 3) is a matrix consisting of a 3×1 tiling of copies of $T_{it}$ (k+1). Now that a new value for $P_{k+1}$ is obtained, new estimates for R and T are calculated using equation (6), i.e. the new estimates, $R_{k+1}$, and $T_{k+1}$ are found with $$\arg\min_{R_{k+1}=R, T_{k+1}=T} f(R, T, Q, P_{k+1}).$$

Figure 3:
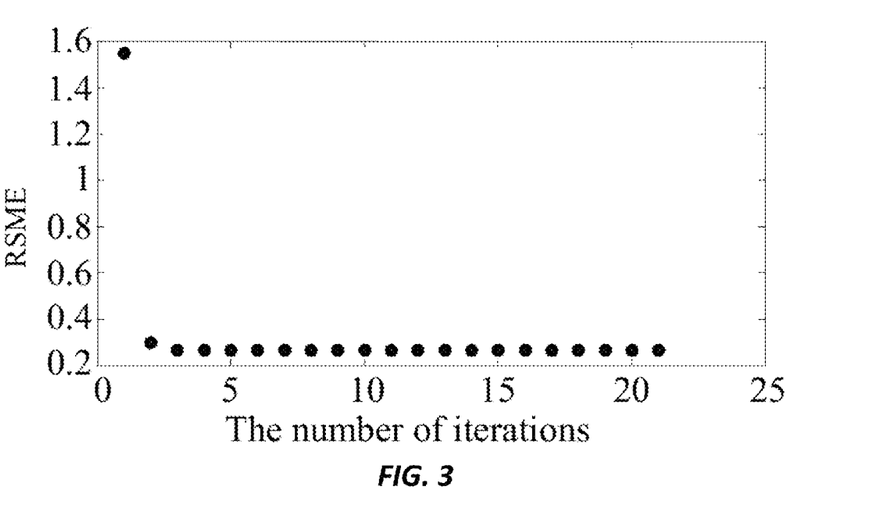
FIG. 3 shows an example of the iterative curves for calculating the rotation matrix using ICP, with the number of iterations 21 and convergence occurring after 3 or 4 iterations, according to one embodiment of the invention.

Convergence usually occurs in fewer than 5 iterations (see FIG. 3 for an example of the error for 21 iterations). In this exemplary implementation at most five iterations were performed and the final value of $P_{k+1}$ is used to estimate the root mean square error (RMSE) of the matrix transformation using equation (10)

$$RMSE = \sqrt{\sum_{i=1}^{N} \frac{(p_{k+1}(i) - q(i))^2}{N}}. \qquad (10)$$

The final step is to calculate the Euler angles, $\theta_{RL}$, $\theta_{SI}$, $\theta_{AP}$, from the rotation matrix, R, using a nonlinear least square fitting algorithm for the new fiducial marker positions.

Figure 4:
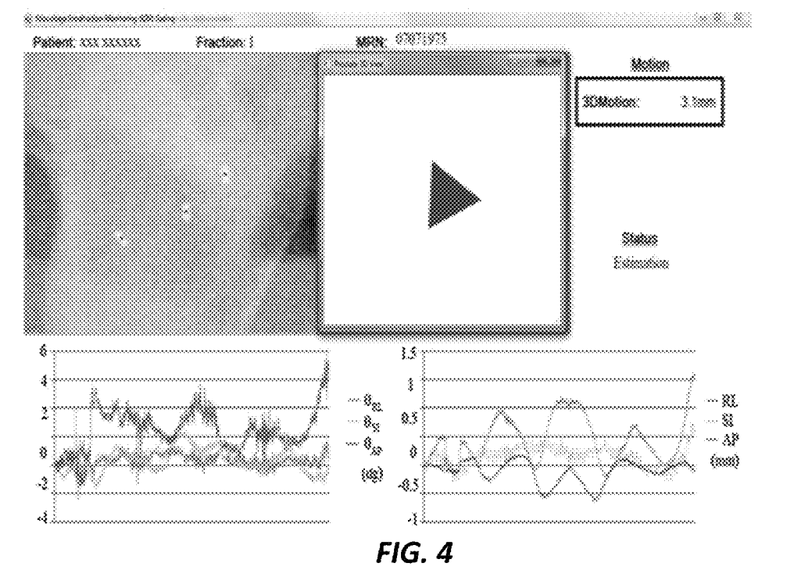
FIG. 4 shows the main screen of the fiducial marker tracking application, where the top left is the latest kilovoltage image showing the segmented marker locations, the middle is a three dimensional view of the markers, and the bottom left the value of the rotation around RL, rotation around SI, and rotation around AP in degrees are shown, the bottom right trajectory of the markers in RL, SI, AP are shown, according to one embodiment of the invention.

A program has been written in C# to show the 3D trajectory of the markers with the rotation calculations as presented in this example. FIG. 4 shows the main screen of the software which shows, in real-time, the latest kilovoltage image with the segmented 2D marker locations, a graphical view of the markers in the middle, the 3D trajectory of the markers and the rotation of the markers.

The analysis of the algorithm in the current invention was started using an example where the rotation values of the markers were known. The performance of the algorithm for prostate cancer patients is analyzed below.

Figure 5:
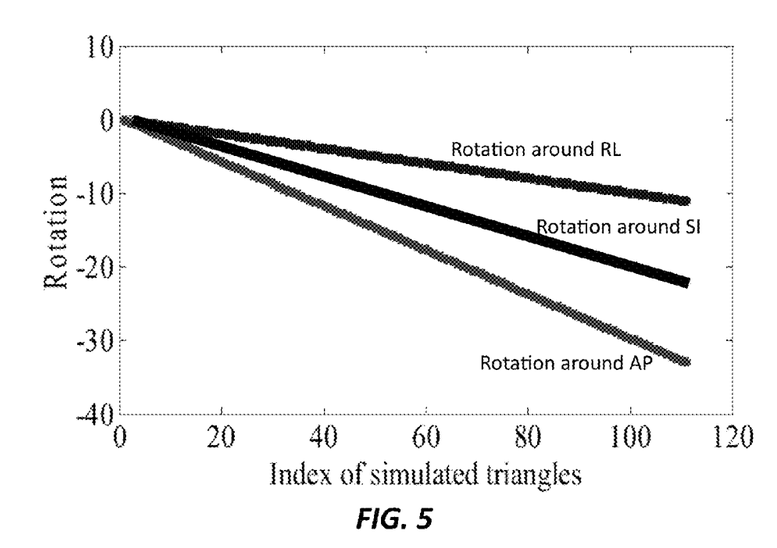
FIG. 5 shows the rotation as computed from the ICP algorithm for a simulated scenario, where the three fiducial markers forming a triangle were rotated by ($\theta_{RL}$=0.1°, $\theta_{SI}$=0.2°, $\theta_{AP}$=0.3°) in each subsequent image, according to one embodiment of the invention.

Regarding the rotation results from ground truth data, in order to evaluate the method, the rotation of three fiducial markers were simulated based on assuming the 3D positions were perfectly estimated. In each simulated image, the triangle formed by the three fiducial markers was rotated in each subsequent image by $\theta_{RL}=0.1°$, $\theta_{SI}=0.2°$, $\theta_{AP}=0.3°$. FIG. 5 shows the value of the rotation around RL, rotation around SI and rotation around AP sequentially.

The mean of the RMSE between the source points and transformed target points (equation (10)) were calculated up to 30°. FIG. 5 shows the linear incremental rotation of up to 30° for three directions. The maximum error up to 30° was 0.007° with a mean value of 0.004°. Rotations of 30° are above the rotations that are observed below for prostate cancer patients.

For prostate rotation results from clinical intrafraction x-ray images the analysis to prostate cancer patients is extended, where the real-time rotation and translation of the prostate for ten prostate cancer patients are calculated. In FIGS. 6(a) and 6(b) an example of the time series of rotation and translation is illustrated for a prostate cancer patient. Rotations of over 7° are observed for this patient. The translation and rotation data are relatively noisy because of the noisy data in the 2D segmented location of the markers. However, a clear trend in the rotation data is visible in FIG. 6(a).

Figure 6:
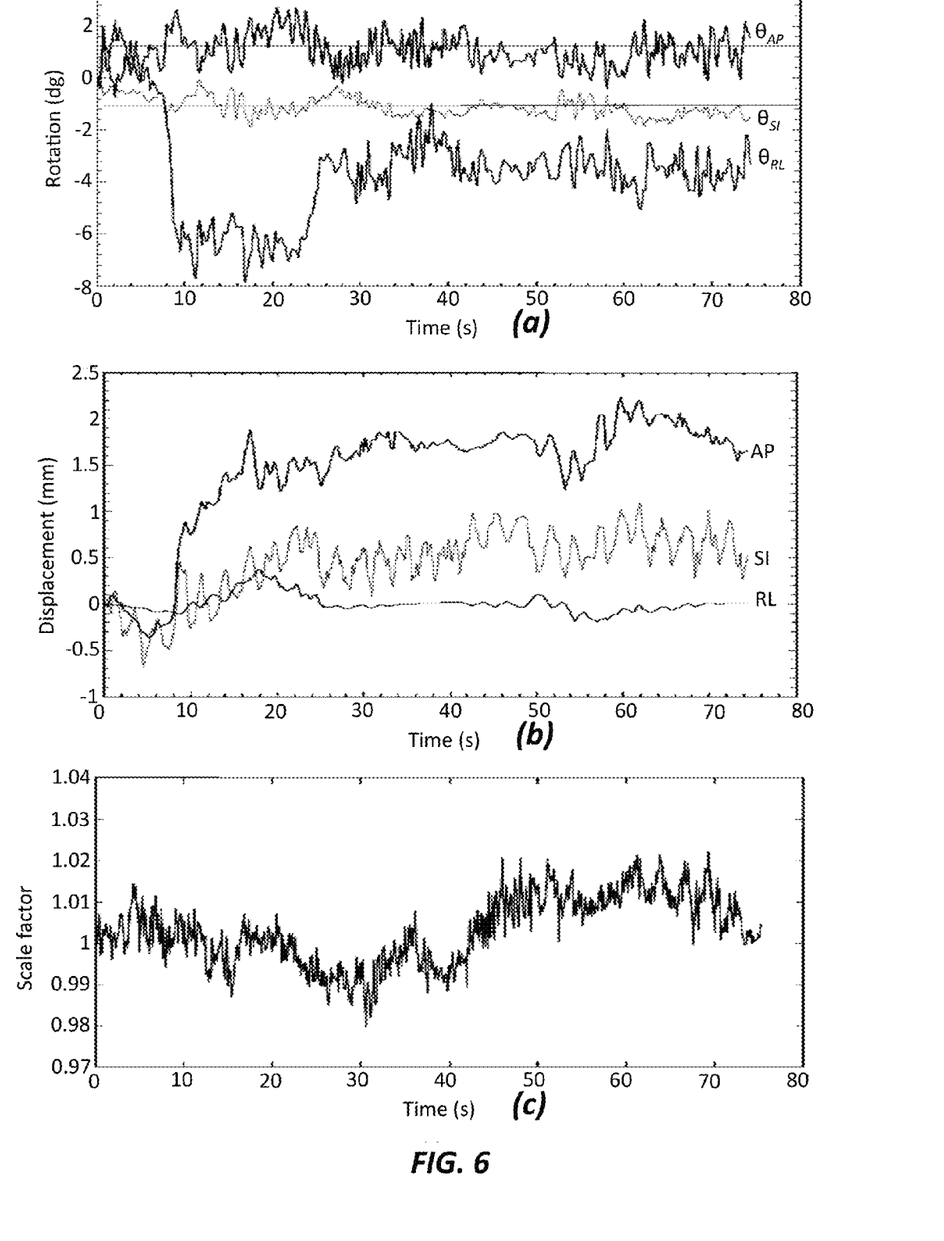
FIGS. 6a-6c show 6(a) an example of prostate rotation angles computed from intrafraction kV images using the ICP algorithm for a prostate cancer patient. The dashed line shows threshold for 1° rotation, 6(b) an example of prostate translation for the same prostate cancer patient, and 6(c) a typical curve of normalized scale factor related to the rigidity of the tumor, according to one embodiment of the invention.
Figure 7:
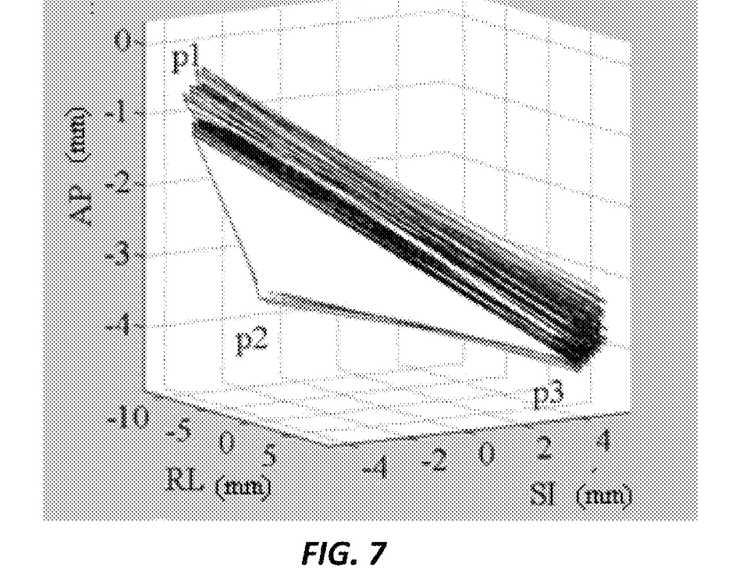
FIG. 7 shows the vertices of the triangle formed by the three fiducial marker locations inside the prostate over time, where the scale factor, s is calculated based on the change in the area of the triangles, according to one embodiment of the invention.
Figure 8:
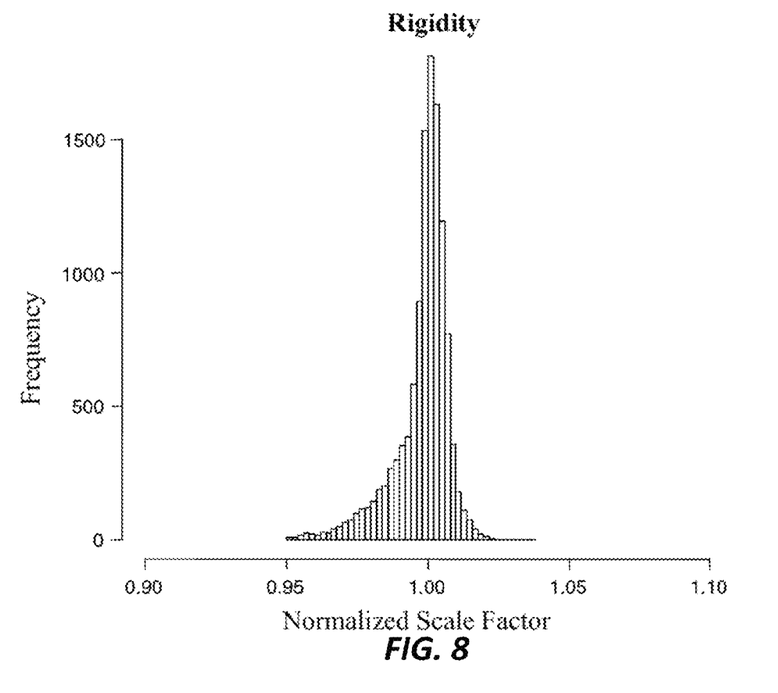
FIG. 8 shows the number of occurrences of the scale factor, s, of the triangles for the 11,748 images acquired from ten prostate cancer patients, according to one embodiment of the invention.
Figure 9A:
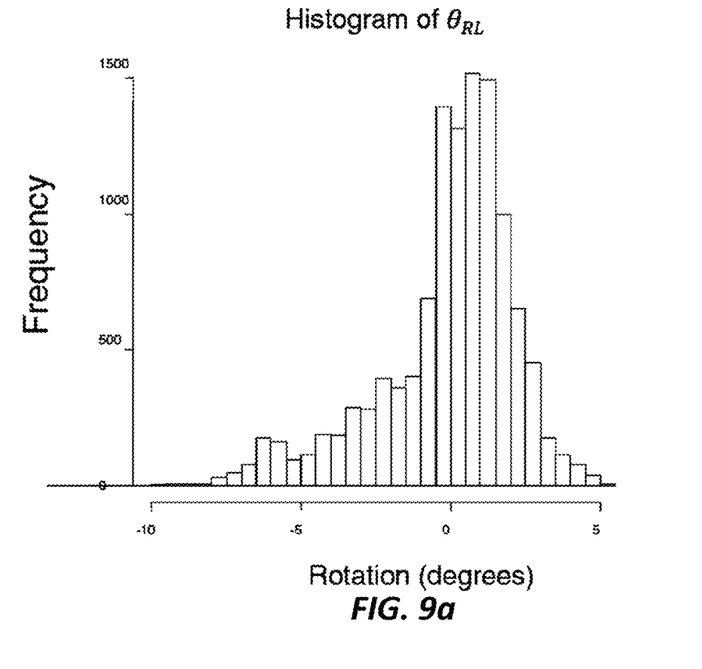
FIGS. 9a-9f show histograms of rotation and translation of the fiducial markers.
Figure 9B:
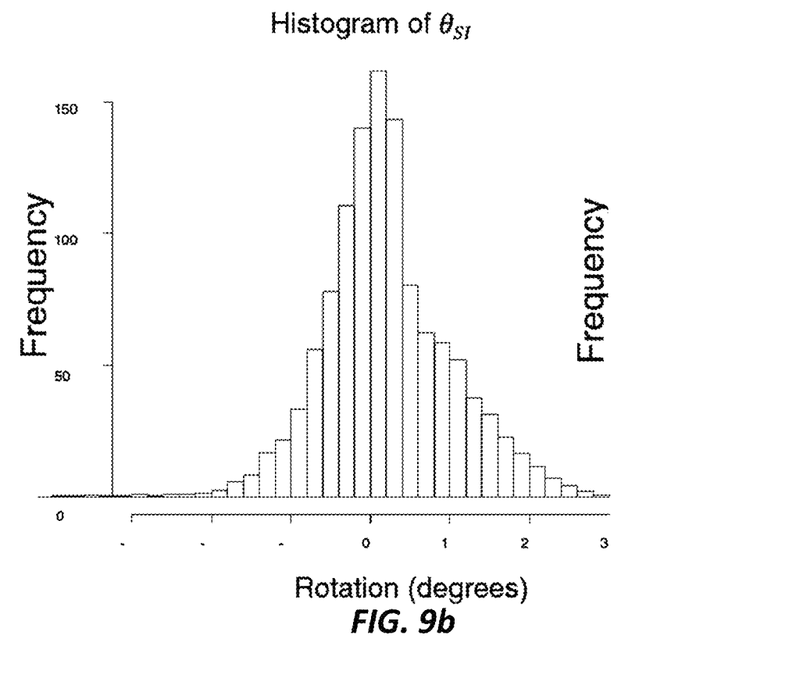
Figure 9C:
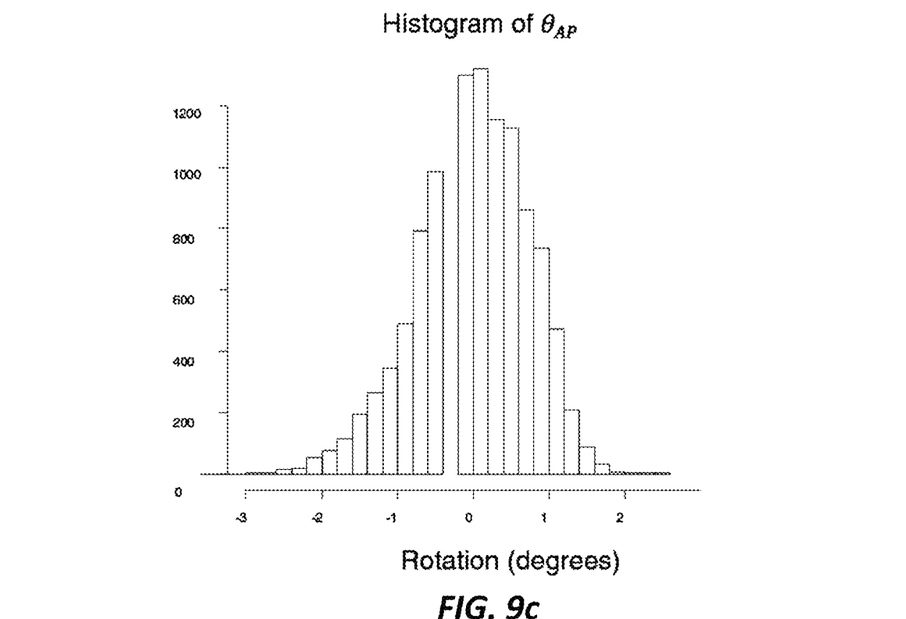
Figure 9D:
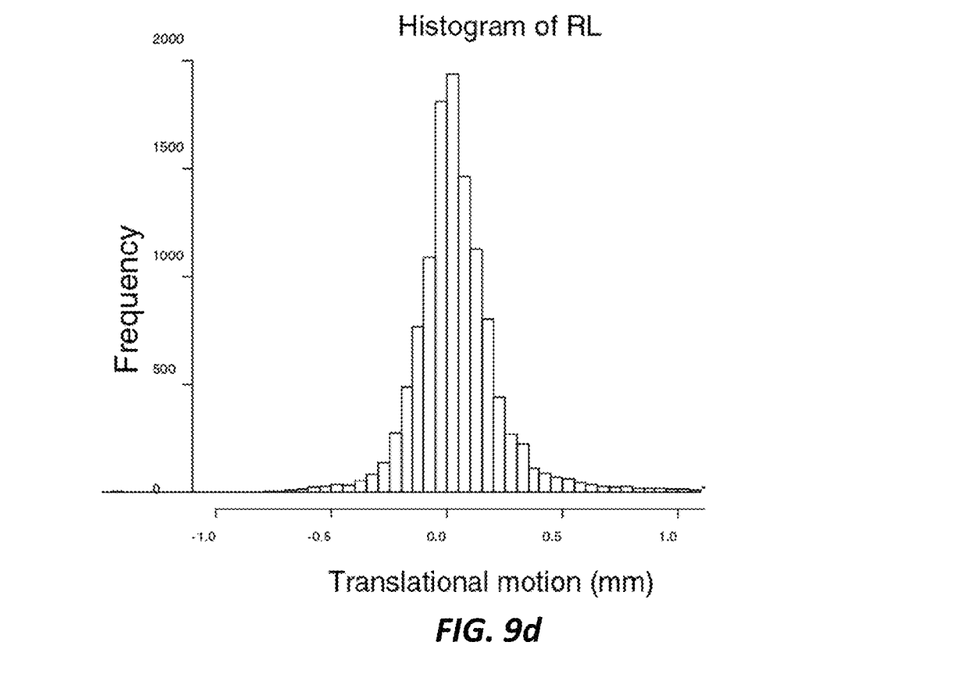
Figure 9E:
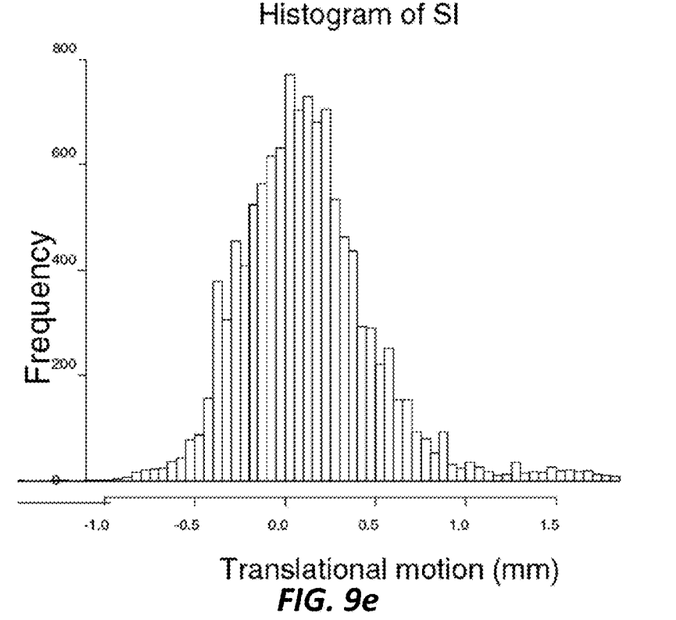
Figure 9F:
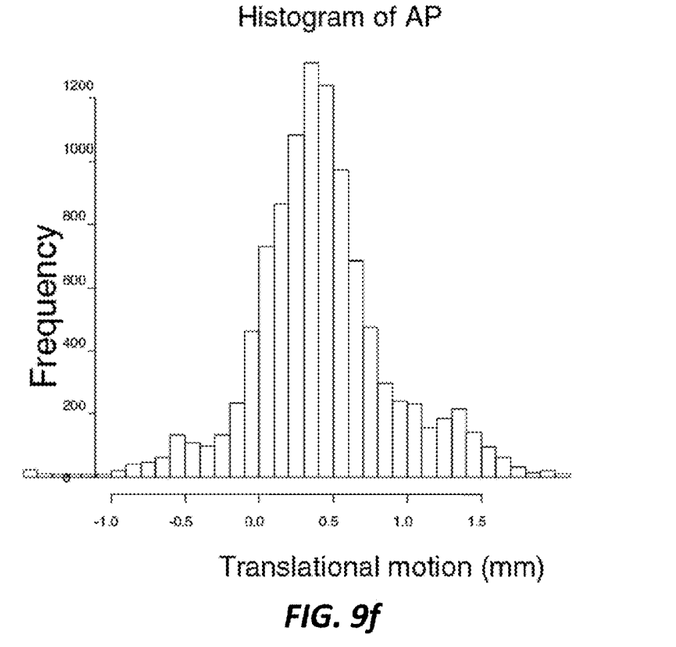
Figure 10:
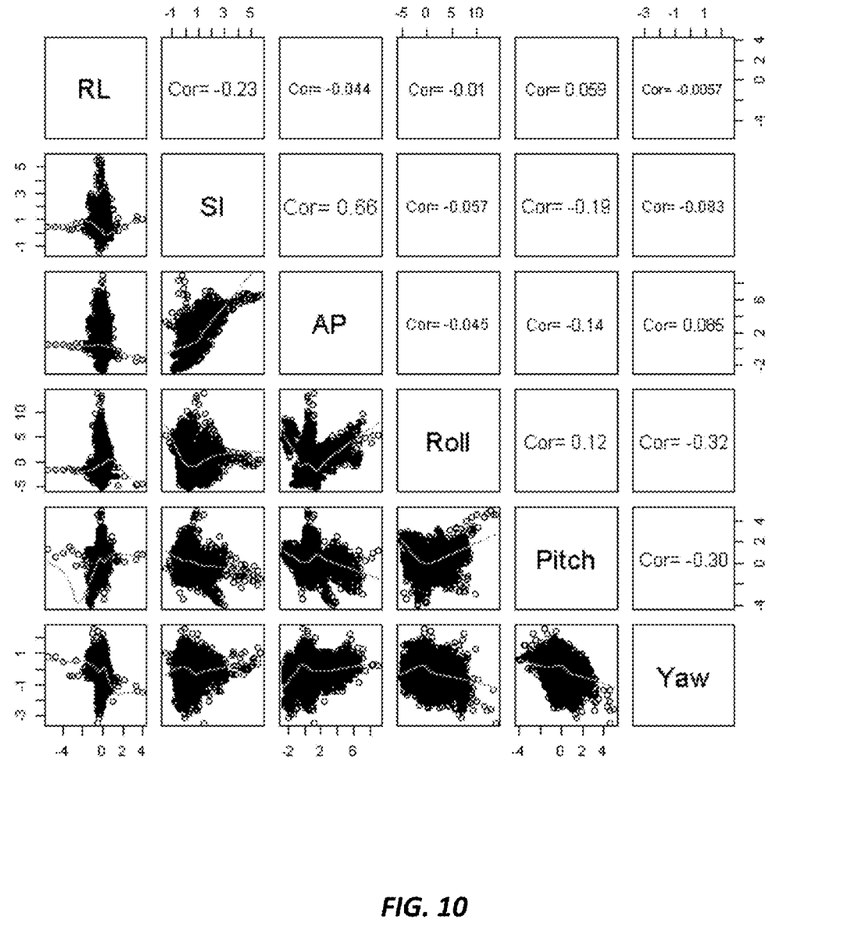
FIG. 10 shows the correlation between translations and rotations for 11,748 images. The white lines are the nonlinear curve fitting using lsqcurvefit (Matlab function) to the data, according to one embodiment of the invention.

FIG. 6(c) shows variations in the scale factor, s, for the same patient. The scale factor was calculated based on the changes in the area of the triangles formed by the three fiducial markers relative to the area of the triangle in the first image. FIG. 7 gives a graphical view of the triangle formed by the markers. FIG. 8 shows the variation of the scale factor for the whole dataset (11,748 images). The correlation coefficient of the template based marker segmentation and scale factors were implemented to detect and remove noise in the rotation calculations. In this example, the threshold for correlation was 0.65 and the threshold for the scale factor set for values with more than a 5% change in size (s=1±0.05). Less than 2% of the data were removed based on these thresholds. FIG. 9 shows the histogram of the translation and rotation parameters. For rotation, the center of $\theta_{RL}$ was around 1°, while $\theta_{SI}$ and $\theta_{AP}$ were centered around 0°. For translation, the SI and RL histograms are centered close to 0 mm, while the center of the AP histogram was around 0.3-0.4 mm. FIG. 10 shows the pair-to-pair data points and the correlation of the variables to each other in the upper right hand triangle. The maximum correlation was between SI and AP translations with a correlation coefficient of 0.66. The correlations between $\theta_{RL}$, $\theta_{SI}$ and $\theta_{AP}$ also had values higher than 0.1 with a negative correlation between $\theta_{RL}$ and $\theta_{AP}$. FIG. 10 also shows that the correlation between $\theta_{SI}$ and $\theta_{AP}$ was almost two times larger than correlation between $\theta_{RL}$ and $\theta_{SI}$.

Figure 11A:
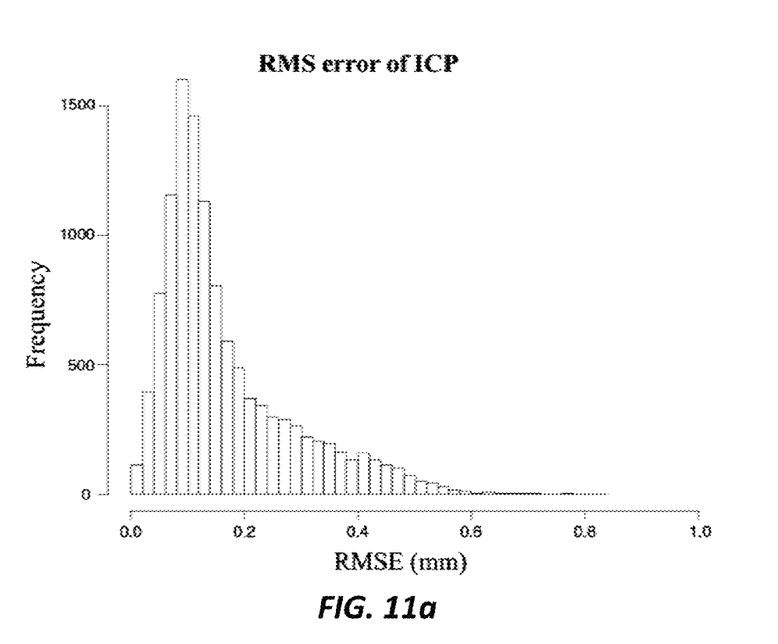
FIGS. 11a-11b show 11(a) RMSE values of translation and rotation with ICP after 20 iterations of the ICP algorithm, 11(b) error of translation.
Figure 11B:
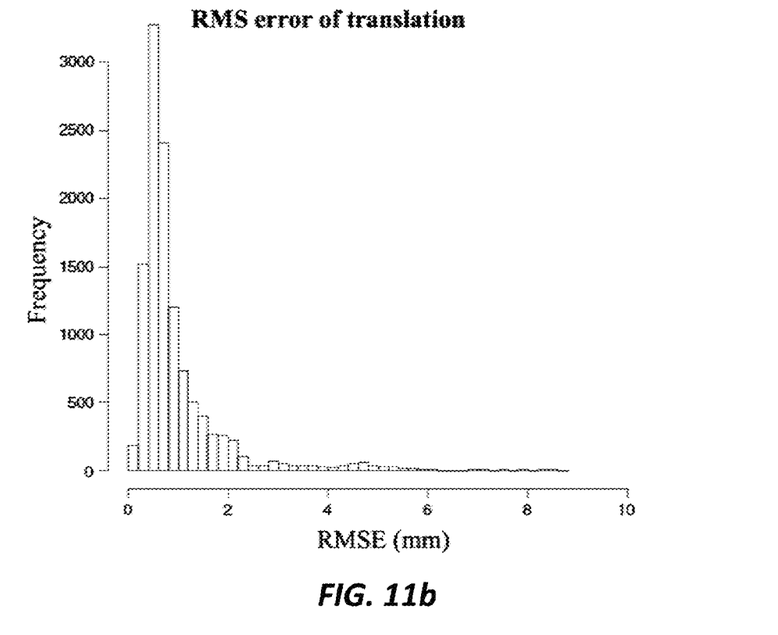

In TABLE 1 the value of SD of rotation and translation is given in millimeters and degrees, respectively. The maximum value of SD is $\theta_{RL}$ with 2.3° of rotation. FIG. 11 shows the RMSE values between the source points and transformed target points (equation (10)) of the rotation with the ICP method. The x-axis shows the distance error of the transformed points using the new rotation matrix R and translation vector T. The mean, median and SD of the errors is given in TABLE 2. The ICP algorithm had a sub-0.2 mm mean, median and SD.

TABLE 1

Standard deviation of rotation and translation

| $\theta_{RL}°$ | $\theta_{SI}°$ | $\theta_{AP}°$ | RL (mm) | SI (mm) | AP (mm) |
|---|---|---|---|---|---|
| 2.26 | 0.89 | 0.72 | 0.32 | 0.53 | 1.13 |

TABLE 2

Mean and standard deviation error of iterative closest point (ICP) algorithm.

| | Mean | SD | Median |
|---|---|---|---|
| ICP error | 0.16 mm | 0.11 mm | 0.12 mm |

In this example, the ICP algorithm was evaluated for real-time estimation of rotation during external beam radiation treatment. Real-time rotation was estimated from three fiducial markers located inside the prostate. The results show that the ICP algorithm converged after two or three iterations to the minimum value. The RMSE deviation of the ICP algorithm was compared with the RMSE error of the displacement using standalone translation and the result showed significant improvement. The additional computation of rotation only adds a few milliseconds to the time used for marker segmentation and 3D position estimation, which is approximately 30 ms. Therefore it is expected the total latency of a real-time clinical rotation estimation system to be less than 300 ms, similar to that measured in end-to-end experiments of kV-image based translation tracking.

Increasing the number of fiducial markers could reduce the value of the RMS error. At present, three fiducial markers are typically implanted in clinical prostate treatments. One of the future directions for this study could be a study of the RMS error for three to five fiducial markers on a phantom to investigate whether the RMS error of translation residual error can be further reduced. Further study on a phantom and a large clinical data set will be used to improve the three dimensional Gaussian PDF to a six dimensional PDF. An additional step required for a clinical implementation would be to use the marker positions from the planning CT scan as the source points rather than those from the pretreatment arc. This would enable the absolute rotational pose from the plan to be computed.

For transforming the rotation matrix to Euler angles, the order of rotation around the axes was selected as RL, SI, and AP respectively. The reason for this choice is that the Euler angles are more understandable from a clinical perspective than other choices such as unit quaternions. The order of rotation around the axes could affect the final value of rotation. However, in this example, the rotation of prostate was mostly less than 10° with RL having the dominant rotation. The order in which rotation around the axes is selected has little effect. For larger rotations, the choice of the order of rotation needs to be considered.

A sensitivity analysis of the effect of marker segmentation error and the impact of the use of the PDF to generate the 3D translation values will form the basis of further work using a larger clinical dataset. From the current results (FIG. 6) it appears the marker segmentation adds approximately 1° of noise to the rotational estimates. This noise could be reduced through improved marker segmentation algorithms and/or signal processing methods such as trend filtering and incorporating mechanical constraints based on known maximum organ translation and rotation.

There are several natural extensions of the current framework to be explored. (1) As the scale factors of the triangles formed by the markers are computed as part of the ICP algorithm, some estimate of target deformation may be possible, or this information used as a warning indicator for potential changes during treatment. (2) The algorithm currently ignores information from the megavoltage (MV) beam. Even for modulated beams some of the markers may be visible for some of the time. The use of the MV image information could be used to augment the kV information. Alternatively, in some situations the ICP method could be implemented with the MV beam alone. (3) A disadvantage of kV intrafraction monitoring is the increased x-ray imaging dose. To reduce the dose, for tumor sites with a respiratory motion component, the kV information could be augmented by a respiratory signal through an internal-external model.

The following describes the method for calculating the rotation matrix, R, and the translation vector T. Let $q_i$ and $p_i$ for i=1, 2, . . . , N denote the location of the N fiducial markers in time $t_1$, and $t_k$, respectively. The centroid of the system of markers is $$\bar{p} = \frac{1}{N} \sum p_i$$

$$\bar{q} = \frac{1}{N} \sum q_i.$$

The deviations from the centroid are given by $p'_i = p_i - \bar{p}$, and $q'_i = q_i - \bar{q}$.

The translation vector T should be chosen to move the centroid of the target dataset to the centroid of the source dataset:

$T = \bar{q} - R\bar{p}$

Substituting the equations for $p'_i$ and $q'_i$ in equation (6) and after some simplification one has $$f(R, T) = \sum_{i=1}^{N} \|p'_i\|^2 - 2tr\left(R \sum_{i=1}^{N} p'_i q'^T_i\right) + \sum_{i=1}^{N} \|q'_i\|^2,$$

where the trace of a matrix A is the sum of the diagonal elements of A: $tr(A) = \sum_{i=1}^{N} a_{ii}$. For convenience set $M = \sum_{i=1}^{N} p'_i q'^T_i = [c_1, c_2, \ldots, c_N]$, and $R = [r_1, r_2, \ldots, r_N]$ where $c_i$ and $r_i$ are the column vectors of M and R respectively. The trace tr (MRN) is maximized in order to minimize f(R, T):

$$tr(RM) = \sum_{i=1}^{3} \sqrt{r_i c_i} \leq \sum_{i=1}^{3} \sqrt{r_i c_i}.$$

Since the rotation matrix R is orthogonal by definition, its row vectors all have unit length.

$$tr(RM) \leq \sum_{i=1}^{3} \sqrt{c_i^T c_i} = \sum_{i=1}^{3} \sqrt{M^T M}.$$

The singular value decomposition of $N = U \Sigma V^T$ ensures that the algorithm always provides the rotation matrix and not the reflection matrix. Finally, R can be calculated using $R = V * \text{diag}([1 1 \det(UV^T)]) * U^T$ where diag is the diagonal matrix and det is the determinant of the matrix.

A method of real-time estimation of prostate tumor rotation and translation (6D) using a single imager kilovoltage intrafraction monitoring has been provided.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example: Principal component analysis alignment (PCA), Singular value decomposition alignment (SVD), and Iterative closest point alignment (ICP).

All such variations are considered to be within the scope and spirit of the present invention as defined by the following claims and their legal equivalents.

What is claimed:

1. A method of real-time estimation of target rotation and translation in 6 degrees of freedom, comprising:
   a. using an x-ray imager, during radiation treatment delivery, to acquire sequential images of the projected 2D positions of at least three fiducial markers implanted in a host, wherein a series of said fiducial markers in 2D images are determined;
   b. determining, using an appropriately programmed computer, a covariance matrix of said fiducial marker locations and mean point fiducial marker locations by fitting a probability distribution function (PDF) to said series of fiducial marker locations in 2D images using a maximum likelihood estimation, wherein said series of fiducial markers location in 2D images are used to determine projected 3D points of said at least three fiducial markers in said host;
   c. inputting said projected 3D points of said at least three fiducial markers to an iterative closest point (ICP) algorithm using said appropriately programmed computer to determine a real-time target rotation and translation about a center of mass of said at least three fiducial markers; and
   d. outputting 3D locations of said at least three fiducial markers rotated around a right-left direction, an anterior-posterior direction, and a superior-inferior direction of said host.

2. The method of real-time estimation of target rotation and translation in 6 degrees of freedom according to claim 1, wherein said ICP algorithm comprises:
   a. creating pairing, using a nearest neighbor algorithm on said appropriately programmed computer, between a set of target points of at least three fiducial markers and a set of source points of said at least three fiducial markers using K nearest neighbors, wherein said source points are determined during a pretreatment arc that is used to build said PDF for said translation and said rotation estimation prior to turning said treatment beam on;
   b. iteratively executing the following:
      i. estimating a rotation parameter R and a translation parameter T of said at least three fiducial markers using a root mean square cost function;
      ii. terminating the estimation of R and T when the change in a mean distance between said set of target points of said at least three fiducial markers and said set of source points of said at least three fiducial markers is below a threshold or at maximum iteration number;
      iii. transforming said set of target points of said at least three fiducial markers using estimated parameters; and
      iv. re-associating a new set of said target points of said at least three fiducial markers.

3. The method of real-time estimation of target rotation and translation in 6 degrees of freedom according to claim 1, wherein said at least three fiducial markers are disposed in a non-linear arrangement.

4. The method of real-time estimation of target rotation and translation in 6 degrees of freedom according to claim 1, wherein said source points of said at least three fiducial markers are generated at time $t_1$ by imaging said at least three fiducial markers using a kilovoltage imager mounted on a rotating gantry disposed to capture two-dimensional images of said at least three fiducial markers, wherein a source position of said at least three fiducial markers is estimated using a said PDF on said two-dimensional images of said at least three fiducial markers, wherein a translation and rotation of said at least three fiducial markers are estimated using said PDF.

5. The method of real-time estimation of target rotation and translation in 6 degrees of freedom according to claim 1, wherein said target points of said at least three fiducial markers are generated at time $t_k$ by i) translating said source points of said at least three fiducial markers along an axis with an unknown transformation function using a translation vector T or ii) rotating said source points of said at least three fiducial markers around an axis with using a rotation matrix R or i) and ii), wherein a set of source points, one for each said fiducial marker, are denoted by $Q=(q_1, q_2, \ldots, q_N)$ and a set of target points, one for each said marker, are denoted by $P=(p_1, p_2, \ldots, p_N)$, wherein N is the number of fiducial markers, wherein when all said markers are translated and rotated by the same amount given by $Q(P)=sRP+T+n$, wherein s is a scaling factor, wherein n is Gaussian noise.

6. The method of real-time estimation of target rotation and translation in 6 degrees of freedom according to claim 5, wherein said scaling factor is determined according to a change in an area defined by said at least three fiducial markers disposed in a non-linear arrangement captured in one 2D kilovoltage (kV) image compared to a subsequent 2D kilovoltage (kV) image.

7. The method of real-time estimation of target rotation and translation in 6 degrees of freedom according to claim 1, wherein said at least three fiducial markers comprise an asymmetric shape.

8. The method of real-time estimation of target rotation and translation in 6 degrees of freedom according to claim 1, wherein said ICP algorithm is executed between one 2D kilovoltage (kV) image and a next 2D kilovoltage (kV) image in a sequence.

9. The method of real-time estimation of target rotation and translation in 6 degrees of freedom according to claim 8, wherein a frequency of said sequential 2D kilovoltage (kV) image is in a range of 0.1-100 Hz.

10. The method of real-time estimation of target rotation and translation in 6 degrees of freedom according to claim 1, wherein said x-ray imager comprises a kilovoltage or megavoltage x-ray imager.

11. The method of real-time estimation of target rotation and translation in 6 degrees of freedom according to claim 1, wherein said fiducial marker positions are used to give an estimate of target deformation.

12. The method of real-time estimation of target rotation and translation in 6 degrees of freedom according to claim 1, wherein a treatment beam is applied to said target in real-time according to said 3D location of said at least three fiducial markers.

* * * * *